United States Patent

Desantis

[11] Patent Number: 5,849,953
[45] Date of Patent: Dec. 15, 1998

[54] PROCESS FOR THE PURIFICATION OF AN INTERMEDIATE

[75] Inventor: Nicola Desantis, Cernusco Sul Naviglio, Italy

[73] Assignee: Fructamine S.p.A., Italy

[21] Appl. No.: 873,771

[22] Filed: Jun. 12, 1997

[30] Foreign Application Priority Data

Jun. 13, 1996 [IT] Italy ................................. MI96A1204

[51] Int. Cl.$^6$ ..................... C07C 231/02; C07C 233/65
[52] U.S. Cl. ..................... 564/153; 424/9.452; 564/142
[58] Field of Search ................... 564/153, 142; 424/9.452

[56] References Cited

U.S. PATENT DOCUMENTS

| | | | |
|---|---|---|---|
| 4,001,323 | 1/1977 | Felder et al. | 424/5 |
| 4,352,788 | 10/1982 | Felder et al. | 424/5 |
| 5,362,905 | 11/1994 | Villa et al. | 560/250 |

*Primary Examiner*—Shailendra Kumar
*Attorney, Agent, or Firm*—Nixon & Vanderhye

[57] ABSTRACT

This invention refers to a new process for the synthesis of (S)-N,N'-bis[(2-hydroxy-1-(hydroxymethyl)ethyl]-5-[(2-hydroxy-1-oxopropyl]amino]-2,4,6-triiodo-1,3-benzendicarboxamide, of formula (III),

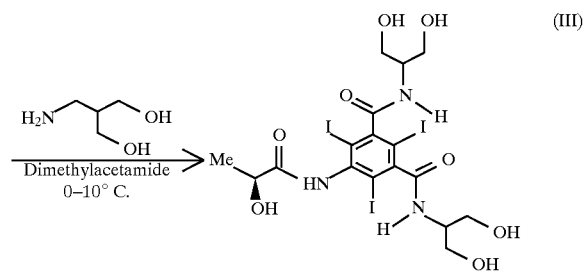

starting from 5-amino-2,4,6-triiodo-1,3-benzendicarboxylic acid dichloride characterized by a new step of chromatographic purification through resins of (S)-5-[[2-(acetyloxy)-1-oxopropyl]amino]-2,4,6-triiodo-1,3-benzendicarboxylic acid dichloride, which enables the direct conversion to the compound of formula (III), without preventive isolation.

12 Claims, No Drawings

PROCESS FOR THE PURIFICATION OF AN INTERMEDIATE

This invention refers to a new process for the synthesis of (S)-N,N'-bis[(2-hydroxy-1-(hydroxymethyl)ethyl]-5-[(2-hydroxy-1-oxopropyl]amino]-2,4,6-triiodo-1,3-benzendicarboxamide, of formula (III), starting from 5-amino-2,4,6-triiodo-1,3-benzendicarboxylic acid dichloride of formula (I) according to Scheme 1, characterized by a new step of chromatographic purification through resins of intermediate (II), (S)-5-[[2-(acetyloxy)-1-oxopropyl]amino]-2,4,6-triiodo-1,3-benzendicarboxylic acid dichloride, which enables the direct conversion to the compound of formula (III), without preventive isolation.

The compound of formula (III), (S)-N,N'-bis[(2-hydroxy-1-(hydroxymethyl)ethyl]-5-[(2-hydroxy-1-oxopropyl]amino]-2,4,6-triiodo-1,3-benzendicarboxamide, better known as Iopamidol is one of the products most widely sold all over the world in the field of X-ray contrast media and its synthesis is described in GB 1472050.

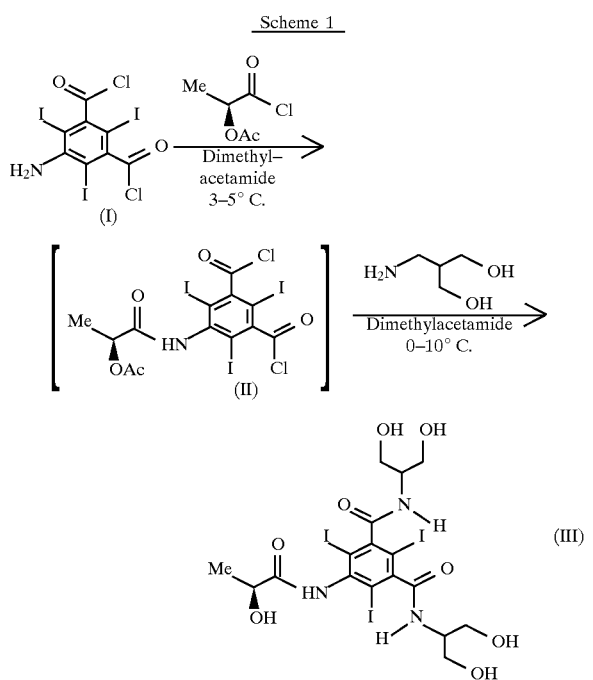

Scheme 1

This synthesis foresees the steps already described in Scheme 1, including, in addition, the isolation of intermediate (II) whose purification is necessary for the following reasons:

- the presence of hydrochloric acid as by-product of the reaction which can react in the successive step with 2-amino-1,3-propandiol (serinol);
- the presence of the excess of (S)-(−)-[2-(acetyloxy)] propionic acid chloride which can react with serinol, too;
- elimination of acid by-products derivatives of amino-2,4,6-triiodobenzoic acid.

An alternative preparation of the intermediate of formula (II) has been recently described in patent application GB 2271990. This patent application overcomes the problem related to a synthetic method which excludes the use of dimethylacetamide (DMA) as solvent by using, in the first step of Scheme 1, a Lewis' acid in catalytic amounts in organic solvents different from dimethylacetamide, in particular, methylene chloride, toluene, 1,2-dichlorethane. Also in this case, the isolation of the compound of formula (II) is needed, which then, as cited by the authors, continues with the procedure described in patent GB 1472050, and illustrated here by Scheme 1, which requires another dissolution in dimethylacetamide in order to react with serinol to give the compound of formula (III).

On the contrary, in the process of this invention, dimethylacetamide is kept, being this one solvent of the successive step and in this way its elimination is unnecessary, thus sparing a synthetic step.

Therefore this invention refers to the process for the preparation of (S)-N,N'-bis[(2-hydroxy-1-(hydroxymethyl)ethyl]-5-[(2-hydroxy-1-oxopropyl]amino]-2,4,6-triiodo-1,3-benzendicarboxamide of formula (III), in a single step according to the above mentioned Scheme 1, comprising the following steps:

a) reaction of the compound of formula (I), 5-amino-2,4,6-triiodo-1,3-benzendicarboxylic acid dichloride with S-(−)-[2-(acetyloxy)]propionic acid dichloride in dimethylacetamide, to give a raw solution of the compound of formula (II), (S)-5-[[2-(acetyloxy)-1-oxopropyl]amino]-2,4,6-triiodo-1,3-benzendicarboxylic acid dichloride, which is purified through elution from porous and/or macroporous cross-linked, anionic and cationic resins;

b) the resulting solution of step a) is added with solid serinol at a temperature of 0°–10° C. and the temperature is maintained for 5–20 h to give the solution in dimethylacetamide of the compound of formula (III), after basic treatment and after removing most of the solvent through distillation and diluted with water.

Using the process of this invention a synthetic step is avoided, which allows the preparation of the compound of formula (III) with a higher yield and in a more profitable way from the industrial point of view. In fact the isolation yield of the compound of formula (II) is substituted with the chemical conversion of the reaction equal to 96% of the compound of formula (II).

The purification through the use of resins does not produce the formation of by-products.

In addition there is an improvement in the industrial production times since the isolation and drying processes and the entire recovery of the solvents in the reaction and precipitation are avoided.

The porous and/or macroporous cross-linked resins used in step a) of the process of this invention, are selected from the group constituted by: anionic cross-linked resins, with a preferable polymer structure of DVB acrylic (divinylbenzene), styrenic DVB, or metaacrylic-DVB, used if anionic, in free base form, if cationic in sodium form.

The resins in step a) can be placed alone or in series, or in mixed bed, in floating bed and the elution is carried out under low or high pressure. The anionic and cationic resins have the following functional characteristics wherein R is generally an alkyl group which varies according to the selected resin type which sometimes cannot be found in the suppliers' catalogue:

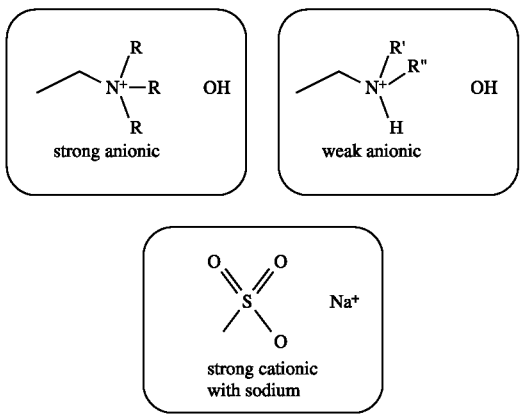

and for instance are supplied by Rhom and Haas as follows:
strong anionic
    Amberlyst$^{(R)}$ A-26, A-29;
weak anionic
    Amberlyst$^{(R)}$ A-21; Amberlite$^{(R)}$ IRA 35;
    Purolite$^{(R)}$ A-830; Amberlite$^{(R)}$ IRA 958;
    Amberlite$^{(R)}$ IRA 904;
cationic
    Amberlyst$^{(R)}$ A-35; Amberlyst$^{(R)}$ A-36;
    Amberlyst$^{(R)}$ XN 1010.

Resins with the same characteristics but supplied by other producers (for instance Lewatit, Dow etc.) can also be used in the process of this invention.

Particularly preferred are the following resins (supplied by Rhom & Haas) and the following arrangement (for the amount of each bed please refer to the Experimental Section):

separate bed: a column containing Amberlyst$^{(R)}$ A-21;

separate bed: a column containing Amberlyst$^{(R)}$ A-21 followed by a second column containing Amberlyst$^{(R)}$ A 26-OH-E;

separate bed: a column containing Amberlyst$^{(R)}$ A-21 followed by a second column containing Amberlite$^{(R)}$ IRA 35;

mixed bed Amberlyst$^{(R)}$ A-21 and A-26-OH;

floating bed Amberlyst$^{(R)}$ A-26-OH-E with solution bottom loading;

floating bed Amberlite$^{(R)}$ IRA 35 with solution bottom loading;

separate bed: a column containing Amberlyst$^{(R)}$ A-21 followed by a second column containing Amberlyst$^{(R)}$ A-26-OH-E followed by a column Amberlyst$^{(R)}$ A-35 sodium regenerated.

It is important to hydrolyze S-(-)-[2-(acetoxy)]propionic acid chloride in excess with water to obtain the corresponding acid and hydrochloric acid, so that the by-products can be kept on the chromatographic columns.

This operation can be carried out by exploiting the residual water present in the resin or by adding a water content which can trigger the hydrolytic process which will continue on the resins.

In fact, despite the production of water, caused by the desalinization of the anionic resin, in some cases it is preferable to trigger the hydrolysis before the step on resins.

The amount of water necessary for this reaction ranges from 0 to 4 g for 100 g of the final reaction solution of the compound of formula (II). The molar amount of necessary water is calculated on the molar excess of S-(-)-[2-(acetoxy)]propionic acid added for the reaction to which the residual water content kept by the resin is subtracted.

The amount of residual water on the resin can be calculated on the amount of water in the solvent used for the conditioning of the same.

It is extremely important to obstacle an excess of water content to avoid the hydrolysis triggering of the acyl chlorides of the compound of formula (II) due to the alkalinity of the functional groups of the anionic resins.

Therefore the water amount must be calculated according to the type of resin used. Anyway the final solution obtained after chromatographic purification must have a residual water content of 0–2% to avoid that the addition of serinol triggers the hydrolysis of the solvent or a part of the compound of formula (II) due to serinol basicity.

This anhydrification can be carried out through undervacuum distillation or by keeping the solution at the foreseen water limits.

In addition the resins used in the process of this invention are particularly useful for the purification of dipolar aprotic organic solvents as for instance dimethylformamide, N-methylpyrrolidone, acetamide, dimethylsulphoxide, acetonitrile and in particular dimethylacetamide or ester derivatives such as butyl acetate, ethyl acetate, amyl acetate or isoamyl acetate.

In fact this solvent can be purified from organic and inorganic iodinated pollutants thanks to the use of porous/macroporous resins with an acrylic, metaacrylic and styrenic polymer structure.

This technique is particularly useful in the case where the solvent pollutants are organic and inorganic salts and the hydrolysis products of the same solvent. Particularly useful is the use of such techniques for the solvent recovery in the synthesis of iodinated contrast media where the solvent residual by-products can be easily removed, thus avoiding complex extractions or concentration and rectification systems and where the solvent quality must be extremely high.

In addition this process is particularly useful in the final removal of residual substances in any solvent without performing rectifications which inevitably reduce the recovery yields due to the elimination of the first fraction condensed and the tail residual fraction in the reboiler.

The resins can be used in anionic/cationic mixed bed or in sequence of separate beds. In this case cationic resins are used in a acid form while anionic resins are used as free base.

Particularly preferred are the following resins and arrangement:

mixed bed Amberlyst$^{(R)}$ A-35 and A-26-OH E;

a column Amberlyst$^{(R)}$ A-35, a column Amberlyst$^{(R)}$ A-29-OH and a column Amberlyst$^{(R)}$ A-35.

In this way a solvent with no residual substances content starting from solutions containing 0.1%–4% (w/w) of inorganic chlorides and other ionic impurities can be obtained.

The resins can be used with organic or hydroorganic solutions with a water content ranging from 0.5% (w/w) to 90% (w/w).

The solvent purification can be monitored through a conductimeter to detect the resin activity during the process.

In this case the value of specific conductivity referred to 25° C., shifts from values of 20–25 mS/cm to <2 μS/cm.

The resulting solvent is then anhydrified through distillation of residual water.

The following examples are aimed at illustrating the best experimental condition to carry out the process of this invention.

EXAMPLE 1

(S)-N,N'-bis[[2-hydroxy-1-(hydroxymethyl)ethyl]]-5-[(2-hydroxy-1-oxopropyl]amino]-2,4,6-triiodo-1,3-benzendicarboxamide.

A) Preparation of a raw solution of (S)-5-[[2-(acetyloxy)-1-oxopropyl]amino]-2,4,6-triiodo-1,3-benzendicarboxylic acid dichloride in DMA.

700 g of (S)-(−)-5-amino-2,4,6-triiodo-1,3-benzendicarboxylic acid dichloride (prepared according to the procedure described in patent GB 1472050) are dissolved, at room temperature and under stirring, in 1 kg of dimethylacetamide.

288 g of (S)-(−)-[2-(acetyloxy)]propionic acid chloride (prepared according to the procedure described in GB 1472050) are added in 4 h and the temperature is maintained at 3°–5° C. The reaction terminates after being kept for 30–40 h at a temperature of 6°–15°.

B) Preparation of a raw solution of (S)-N,N'-bis[[2-hydroxy-1-(hydroxymethyl)ethyl]-5-[(2-hydroxy-1-oxopropyl]amino]-2,4,6-triiodo-1,3-benzendicarboxamide.

680 g of a 42% (w/w) solution A) are filtered to remove the precipitated DMA hydrochloride and then diluted with 310 g of DMA. 3.5 g of deionized water are loaded to trigger the hydrolysis of (S)-(−)-[2-(acetyloxy)]propionic acid chloride, and the mixture is kept under stirring for 30'. The resulting solution is percolated on 1200 ml of anionic resin Amberlyst$^{(R)}$ A-21 with an exchange capacity of 1.25 eq/L, previously anhydrified.

The resin is washed with 1000 ml of anhydrous DMA and the resin residual product is completely removed. DMA is distilled under vacuum at 70° C. and 12 mmHg in order to give a 20% (w/w) solution of (S)-5-[[2-(acetyloxy)-1-oxopropyl]amino]-2,4,6-triiodo-1,3-benzendicarboxylic acid dichloride equal to 1430 g.

152.3 g of solid serinol (commercial product) are loaded and the temperature is kept under 5° C. When the addition terminates the reaction mixture is kept under stirring for 8 h at 10° C. Most of the reaction solvent is distilled at 95° C. and 10 mbar to give a viscous residue, which is diluted under heating with deionized water.

The temperature of the resulting solution, containing more than 99% of the theoretical product, is raised to 35° C. 120 g of 30% w/w sodium hydroxide are added and kept under stirring for 7 h to produce the saponification of acetic ester of the desired product, that's to say (S)-N,N'-bis[(2-hydroxy-1-(hydroxymethyl)ethyl]-5-[(2-acetyl)-1-oxopropyl]amino]-2,4,6-triiodo-1,3-benzendicarboxamide. Then 50 g of 34% w/w hydrochloric acid are added to keep the pH at 6.5 to terminate the saponification and the resulting solution of the desired raw product is then subjected to the procedure described in patent GB 1472050.

Yield of the compound of formula (III) starting from the compound of formula (I)=75%

EXAMPLE 2

Alternative to EXAMPLE 1.

680 g of the raw solution A) of EXAMPLE 1 are kept for 1 h at 0° C. and then filtered at the same temperature by removing the precipitated DMA hydrochloride, then 410 g of DMA are added. 10.0 g of deionized water are loaded to trigger the hydrolysis of (S)-(−)-[2-(acetyloxy)]propionic acid chloride and the mixture is kept under stirring for 30'.

The resulting solution is percolated on 800 ml of anionic resin Amberlyst$^{(R)}$ A 21 and with an exchange capacity of 1.25 eq/L and 200 ml of strong anionic resin Amberlyst$^{(R)}$ A-26-OH-E with an exchange capacity of 0.8 eq/L constituting a mixed bed of anionic weak/strong resins and 50 ml of cationic resin Amberlyst$^{(R)}$ A-35 with an exchange capacity of 1.9 eq/L regenerated with sodium, previously anhydrified with DMA to give an eluate with 0.5% of residual water.

The resin is washed with 1500 ml of anhydrous DMA and the resin residual product is completely removed.

152.3 g of solid serinol are loaded following the procedure of EXAMPLE 1.

Yield of the compound of formula (III) starting from the compound of formula (I)=80%

EXAMPLE 3

Alternative to EXAMPLE 1.

680 g of the raw solution A) of EXAMPLE 1 are kept for 1 h at −5° C. and then filtered at the same temperature thus removing the precipitated DMA hydrochloride, then 310 g of DMA are added. 2.5 g of deionized water are loaded to trigger the hydrolysis of (S)-(−)-[2-(acetyloxy)]propionic acid chloride and the mixture is kept under stirring for 30'.

The resulting solution is percolated on 800 ml of anionic resin Purolite$^{(R)}$ A-830 with an exchange capacity of 2.7 eq/L previously anhydrified with DMA to give an eluate with 1.5% of residual water. The resin is washed with 1000 ml of anhydrous DMA and the resin residual product is completely removed. DMA is distilled under vacuum at 70° C. and 12 mmHg in order to give a 20% (w/w) solution of (S)-5-[[2-(acetyloxy)-1-oxopropyl]-amino]-2,4,6-triiodo-1,3-benzendicarboxylic acid dichloride equal to 1430 g.

152.3 g of solid serinol are loaded following the procedure of EXAMPLE 1.

Yield of the compound of formula (III) starting from the compound of formula (I)=65%

EXAMPLE 4

Alternative to EXAMPLE 1.

680 g of the raw solution A) of EXAMPLE 1 are kept for 1 h at 0° C. and then filtered at the same temperature by removing the precipitated DMA hydrochloride, then 310 g of DMA are added. 15.0 g of deionized water are loaded to trigger the hydrolysis of (S)-(−)-[2-(acetyloxy)]propionic acid chloride and the mixture is maintained under stirring for 30'.

The resulting solution is fed from the column bottom producing a floating bed of 1500 ml of anionic resin Amberlite$^{(R)}$ IRA 35 with an exchange capacity of 1.0 eq/L. The resin is washed with 1500 ml of anhydrous DMA and the resin residual product is completely removed.

152.3 g of solid serinol are loaded following the procedure of EXAMPLE 1.

Yield of the compound of formula (III) starting from the compound of formula (I)=55%

EXAMPLE 5

Alternative to EXAMPLE 1.

680 g of the raw solution A) of EXAMPLE 1 are kept for 1 h at 0° C. and then filtered at the same temperature thus removing the precipitated DMA hydrochloride, then 310 g of DMA are added. The resulting solution is fed from the column bottom on 1500 ml of anionic resin Amberlite$^{(R)}$ IRA 958 with an exchange capacity of 1.2 eq/L and 300 ml of cationic resin Amberlite$^{(R)}$ IRA 35 with an exchange capacity of 1.25 eq/L previously anhydrified with DMA to give an eluate with 0.5% of residual water. The resin is washed with 1500 ml of anhydrous DMA and the resin residual product is completely removed. DMA is distilled under vacuum at 70° C. and 12 mmHg in order to give a 20% (w/w) solution of (S)-5-[[2-(acetyloxy)-1-oxopropyl]-amino]-2,4,6-triiodo-1,3-benzendicarboxylic acid dichloride equal to 1430 g.

152.3 g of solid serinol are loaded following the procedure of EXAMPLE 1.

Yield of the compound of formula (III) starting from the compound of formula (I)=78%

EXAMPLE 6
Purification of DMA with porous/macroporous cross-linked resins.

5 l of DMA solution di DMA with the following analytical characteristics:
Chlorides=3%
Mixture of 5-amino-2,4,6-triiodo-1,3-benzendicarboxylic acid and by-products of mono- and diiodination=5%
Specific conductivity=24 mS/cm
Water=65%

The solution is percolated on 600 ml of cationic resin Amberlyst$^{(R)}$ A-35, and in series, on 1400 ml of anionic resin Amberlyst$^{(R)}$ A-26-OH-E and on 150 ml of resin Amberlyst$^{(R)}$ A-35.

An eluate with 10 μS/cm is given; no chlorides and no triiodobenzoic acids are present. The solvent is anhydrified through distillation under vacuum up to residue content <0.5%.
Recovery yield >90%

EXAMPLE 7
DMA Purification with porous/macroporous cross-linked resins.

5 l of DMA solution with the following analytical characteristics:
Chlorides=2%
(S)-5-[[2-(hydroxy)-1-oxopropyl]amino]-2,4,6-triiodo-1,3-benzendicarboxylic acid=2%
Specific conductivity=14 mS/cm
Water=5%

The resulting solution is percolated on a mixed bed containing 600 ml of cationic resin Amberlyst$^{(R)}$ A-35 and 1500 ml of anionic resin Amberlyst$^{(R)}$ A 29 to give a residual conductivity of 2.4 μS/cm; no chlorides and no iodophthalic acids are present. The solvent is anhydrified through distillation to give a water content <0.5%.
Recovery yield >90%

I claim:

1. Process for the preparation of (S)-N,N'-bis[(2-hydroxy-1-(hydroxymethyl)ethyl]-5-[(2-hydroxy-1-oxopropyl]amino]-2,4,6-triiodo-1,3-benzendicarboxamide according to Scheme 1, comprising the following steps:

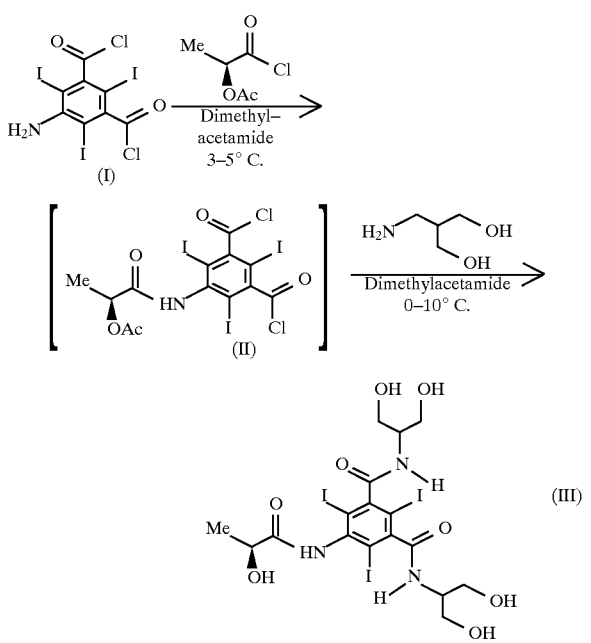

Scheme 1 a) reaction of the compound of formula (I), 5-amino-2,4,6-triiodo-1,3-benzendicarboxylic acid dichloride with S-(-)-[2-(acetyloxy)]propionic chloride in dimethylacetamide in order to give a solution of the compound of formula (II), (S)-5-[[2-(acetyloxy)-1-oxopropyl]amino]-2,4,6-triiodo-1,3-benzendicarboxylic acid dichloride in dimethyl-acetamide;

b) elution of the resulting solution of step a) from porous and/or macroporous cross-linked resins, anionic and cationic, anionic resins as free base form, cationic resins as sodium salt form, with the proviso that the system constituted by said solution and resin contains a water amount which can hydrolyze the excess of S-(-)-[2-(acetyloxy)]propionic acid chloride, but which does not hydrolyze the dichloride of compound (II);

c) possible water elimination from the resulting solution of step b) up to a content of 0–2%;

d) reaction with serinol at a temperature of 0°–10° C. for 5–20 h;

e) isolation of the compound of formula (III).

2. Process according to claim 1, in which in the step a) the polymer structure of porous and/or macroporous cross-linked resins is selected from the group consisting of acrylic-divinylbenzene, styrenic-divinylbenzene, or metaacrylic-divinylbenzene.

3. Process according to claim 1, in which said resins are arranged single or connected in series, or in mixed bed or in floating bed and the elution is carried out under low or high pressure.

4. Process according to claim 3, in which said resin is a weak anionic resin arranged in a separate bed.

5. Process according to claim 4, in which said resins are a weak anionic resin arranged in a separate bed, followed by one strong anionic resin arranged in separate bed.

6. Process according to claim 4, in which said resins are one weak anionic resin arranged in a separate bed, followed by a different weak anionic resin arranged in a separate bed.

7. Process according to claim 4, in which said resins are a weak anionic resin and a strong anionic resin arranged in a mixed bed.

8. Process according to claim 4, in which said resins are a strong anionic resin arranged in a floating bed and the solution is loaded from the column bottom.

9. Process according to claim 4, in which said resins are a weak anionic resin arranged in a floating bed and the solution is loaded from the column bottom.

10. Process according to claim 4, in which said resins are a weak anionic resin, followed by a strong anionic resin, followed by a cationic resin, said resins are arranged in a separate bed.

11. Process according to claim 1, in which the water amount necessary for the hydrolysis of (S)-(-)-[2-(acetyloxy)]propionic acid chloride can be obtained through water addition before elution.

12. Process according to claim 1, in which water elimination in step c) is carried out through under-vacuum distillation.

* * * * *